(12) United States Patent
Sasaki et al.

(10) Patent No.: US 11,458,278 B2
(45) Date of Patent: Oct. 4, 2022

(54) GAS SUPPLY DEVICE FOR RESPIRATION AND CONTROL METHOD THEREFOR

(71) Applicant: Teijin Pharma Limited, Tokyo (JP)

(72) Inventors: Masato Sasaki, Tokyo (JP); Naoyuki Iida, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 515 days.

(21) Appl. No.: 16/489,134

(22) PCT Filed: Mar. 22, 2018

(86) PCT No.: PCT/JP2018/011307
§ 371 (c)(1),
(2) Date: Aug. 27, 2019

(87) PCT Pub. No.: WO2018/180848
PCT Pub. Date: Oct. 4, 2018

(65) Prior Publication Data
US 2019/0388644 A1    Dec. 26, 2019

(30) Foreign Application Priority Data

Mar. 27, 2017 (JP) .............................. JP2017-061658

(51) Int. Cl.
*A61M 16/20* (2006.01)
*A61M 16/00* (2006.01)
*A61M 16/10* (2006.01)

(52) U.S. Cl.
CPC ...... *A61M 16/204* (2014.02); *A61M 16/0003* (2014.02); *A61M 16/101* (2014.02);
(Continued)

(58) Field of Classification Search
CPC .............. A61M 16/204; A61M 16/101; A61M 16/024; A61M 16/202; A61M 16/0677;
(Continued)

(56) References Cited

U.S. PATENT DOCUMENTS

| 5,626,131 A | 5/1997 | Chua et al. |
| 2005/0274381 A1* | 12/2005 | Deane .................. A61M 16/10 128/204.23 |

(Continued)

FOREIGN PATENT DOCUMENTS

| CN | 101543655 A | 9/2009 |
| JP | 01-221170 A | 9/1989 |

(Continued)

OTHER PUBLICATIONS

Communication, dated Mar. 9, 2020, issued by the European Patent Office in European Patent Application No. EP 18 77 7701.

(Continued)

*Primary Examiner* — Margaret M Luarca
(74) *Attorney, Agent, or Firm* — Sughrue Mion, PLLC

(57) ABSTRACT

The device of the invention is equipped with a pressure sensor and a control unit, and the control unit judges a point at which a pressure gradient calculated from a signal of the pressure sensor becomes larger in the absolute value than a pressure gradient threshold as an inspiration sensing point and starts respiratory gas supply. In addition, the device judges from a frequency of the inspiration sensing point during predetermined time whether a pressure gradient threshold used as a criterion for the inspiration sensing point corresponds to an activity state of the user, and when the pressure gradient threshold does not correspond to the activity state, switches the pressure gradient threshold to another threshold and thus fits the pressure gradient threshold to the activity state.

18 Claims, 6 Drawing Sheets

(52) U.S. Cl.
CPC ............ *A61M 2016/0027* (2013.01); *A61M 2016/0039* (2013.01)

(58) Field of Classification Search
CPC ............ A61M 16/022; A61M 16/0051; A61M 16/0069; A61M 16/201
See application file for complete search history.

(56) References Cited

U.S. PATENT DOCUMENTS

| | | | |
|---|---|---|---|
| 2006/0150972 A1 | 7/2006 | Mizuta et al. | |
| 2008/0078392 A1 | 4/2008 | Pelletier et al. | |
| 2012/0055477 A1 | 3/2012 | Wilkinson | |
| 2013/0152933 A1 | 6/2013 | Lischer et al. | |
| 2014/0137859 A1* | 5/2014 | Wilkinson | A61M 16/0051 128/204.23 |
| 2014/0150789 A1* | 6/2014 | Flanagan | A61M 16/104 128/203.22 |

FOREIGN PATENT DOCUMENTS

| | | |
|---|---|---|
| JP | 2656530 B2 | 9/1997 |
| JP | 2002-085568 A | 3/2002 |
| JP | 2004-105230 A | 4/2004 |
| JP | 2015-531308 A | 11/2015 |
| WO | 2005/118038 A2 | 12/2005 |
| WO | 2006/004626 A1 | 1/2006 |
| WO | 2014/059405 A1 | 4/2014 |

OTHER PUBLICATIONS

Communication, dated Jul. 14, 2020, issued by the Japanese Patent Office in Application No. 2019-509640.
International Search Report for PCT/JP2018/011307, dated May 15, 2018.

* cited by examiner

[Fig. 1]
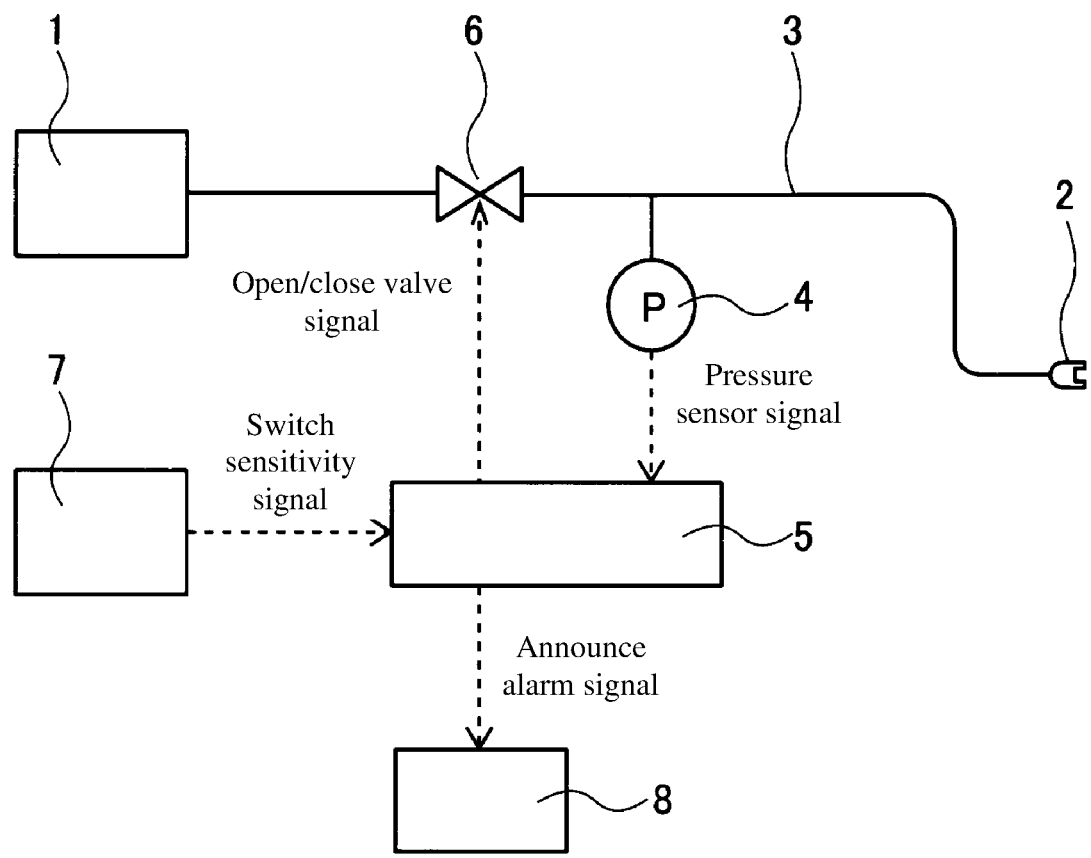

[Fig. 2]
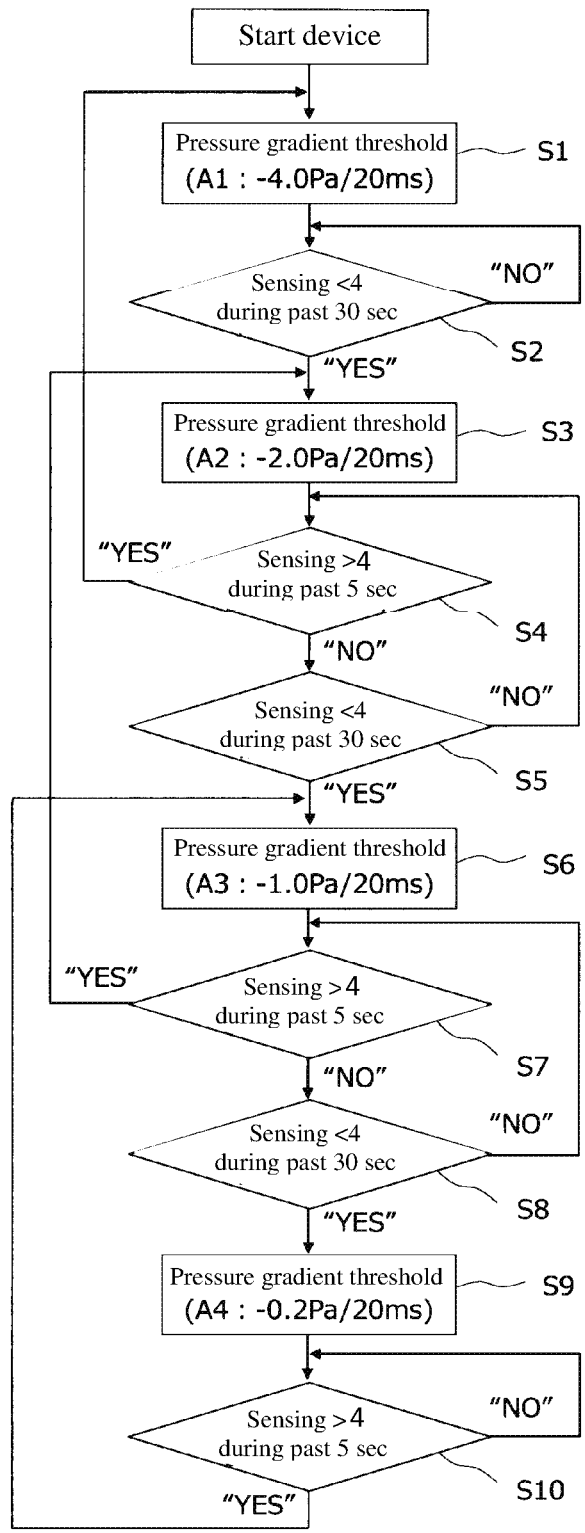

[Fig. 3]
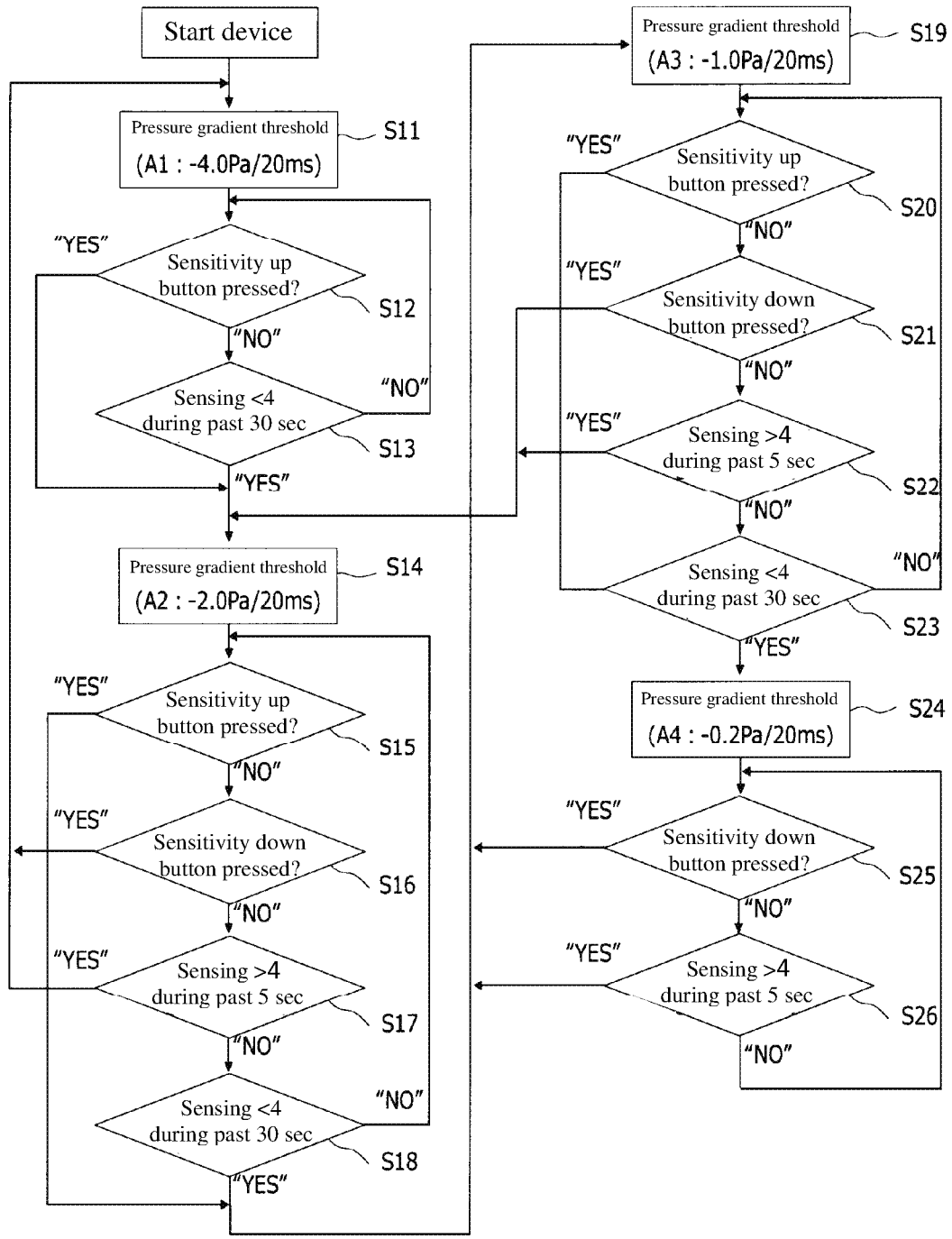

[Fig. 4]
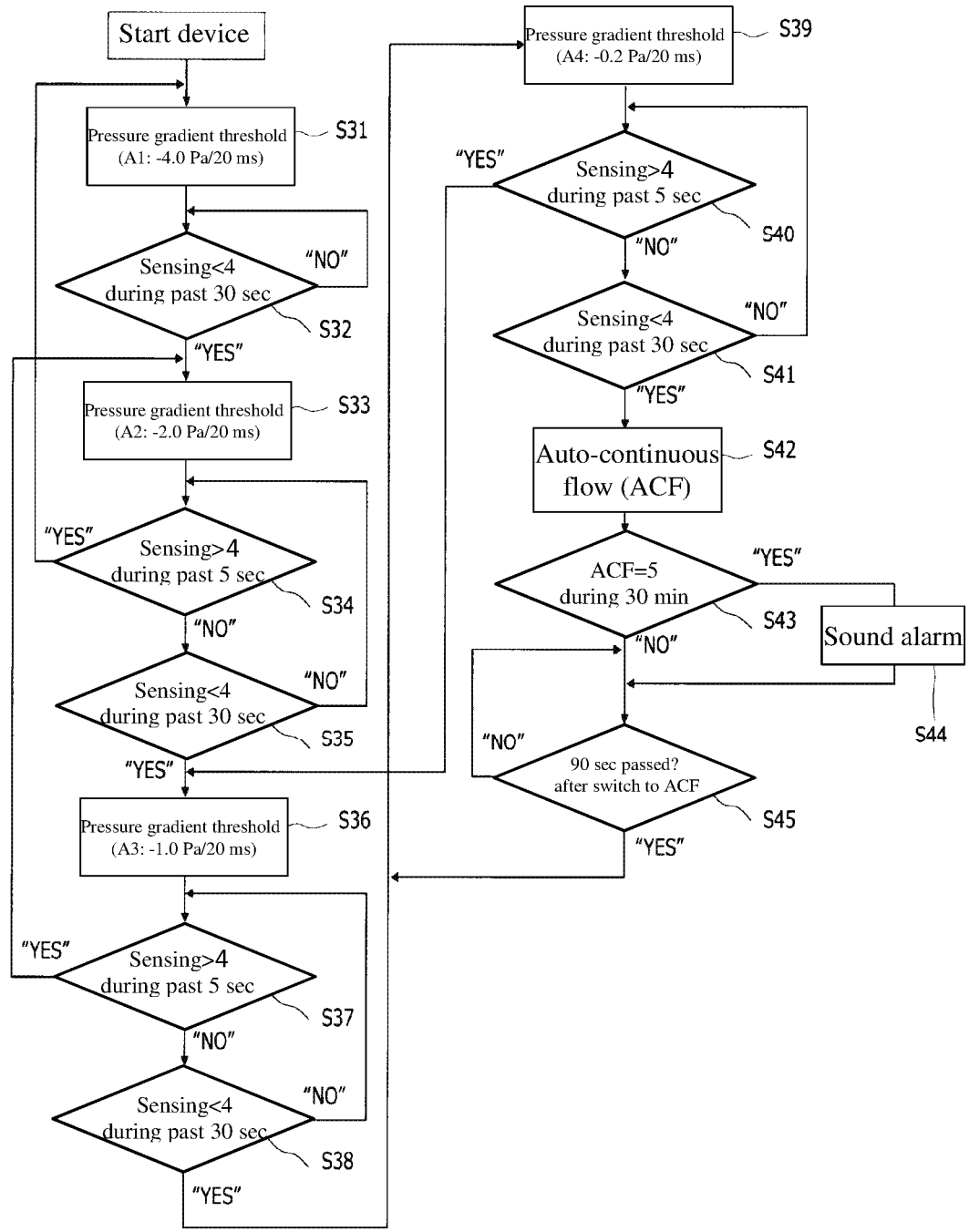

[Fig. 5]
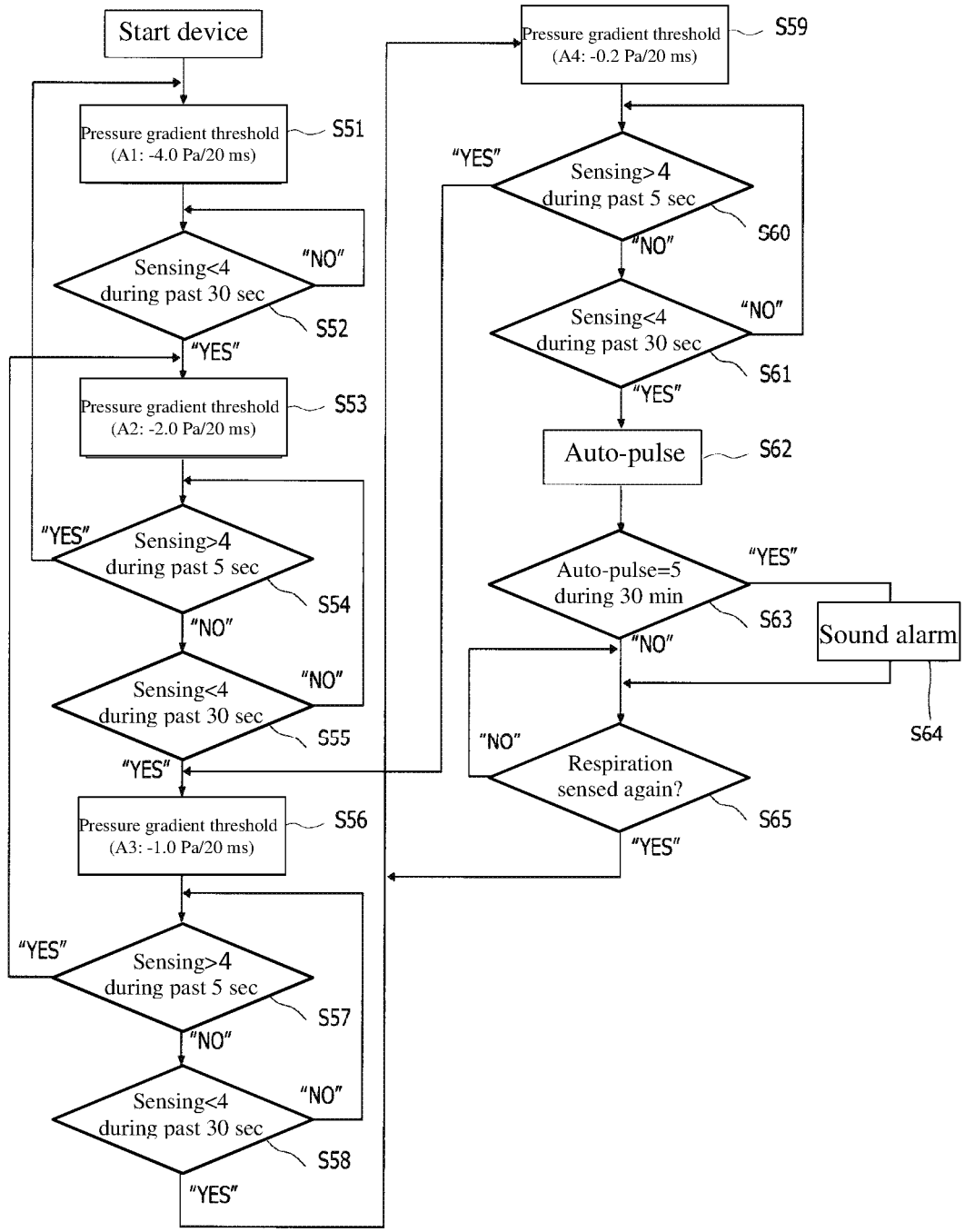

[Fig. 6(a)]
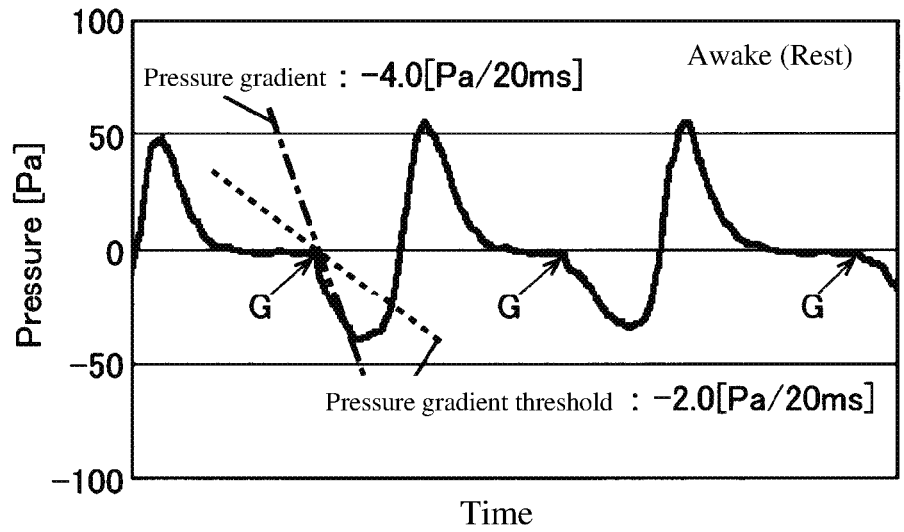
[Fig. 6(b)]
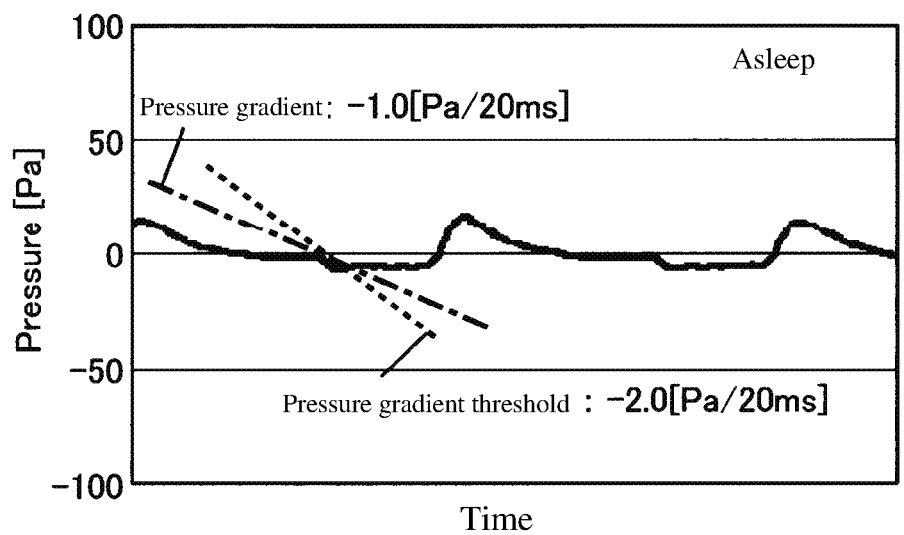

GAS SUPPLY DEVICE FOR RESPIRATION AND CONTROL METHOD THEREFOR

CROSS REFERENCE TO RELATED APPLICATIONS

This application is a National Stage of International Application No. PCT/JP2018/011307 filed Mar. 22, 2018, claiming priority based on Japanese Patent Application No. 2017-061658 filed Mar. 27, 2017.

TECHNICAL FIELD

The present invention relates to a respiration-synchronization type respiratory gas supply device that supplies a respiratory gas such as concentrated oxygen and the like in response to a respiratory cycle of a user, and a control method thereof.

BACKGROUND ART

As a therapy for respiratory diseases such as asthma, emphysema, chronic bronchitis, and the like, an oxygen inhalation therapy is performed to supplement shortage of oxygen by administering a high concentration oxygen gas to a patient for inhalation. A home oxygen inhalation therapy is a therapy in which a patient as a user of the respiratory gas supply device, such as an oxygen concentration device, an oxygen cylinder and the like, operates the device according to the prescription by a physician, and receives the oxygen inhalation therapy at home. Recent development of a portable oxygen concentration device powered by battery and the like has been expanding the application of the respiratory gas supply device.

Many of the portable respiratory gas supply devices are of a respiration-synchronization type equipped with a demand regulator function to feature downsizing, light weighting and long-time operation (PTL 1, 2). The demand regulator function senses the respiratory phase of a user using a pressure sensor and the like, and synchronizes with a respiratory cycle to supply a respiratory gas such as an oxygen gas and the like only during an inspiratory phase and stop supply during an expiratory phase. The function does not supply the respiratory gas continuously, but pulsatively supplies the gas in response to the respiratory cycle of the user, and thus can reduce the consumption of the respiratory gas and electricity.

In order to sense a respiratory phase in the demand regulator function, devised is such a method of equipping a pressure sensor in the gas supply path supplying gas to a cannula and detecting a pressure change accompanying the respiratory phase. Specifically there is a method of judging that an inspiratory phase has started when a measured pressure value by the pressure sensor becomes lower than the predetermined threshold for the pressure value, or when a rate of temporal change of the pressure value (pressure gradient) during a transition from an expiratory phase to an inspiratory phase exceeds the predetermined threshold for a pressure gradient.

Since the pressure sensor used for sensing a respiratory phase has an extremely high detectability, an offset, shift of the reference point of the pressure sensor, due to the influence of the operating environment, such as temperature and the like, and the change over time by the long-term usage becomes a problem. Sensing of the start of an inspiratory phase using a pressure level threshold suffers from an error, delay or the like on sensing the start of an inspiratory phase caused by a shift in the measured value due to the offset. Thus, it is considered a preferable method to sense a start of an inspiratory phase using the pressure gradient threshold that is hardly affected by the offset.

CITATION LIST

Patent Literature

[PTL 1] Japanese Patent No. 2656530
[PTL 2] Japanese Unexamined Patent Application Publication No. 2004-105230

SUMMARY OF INVENTION

Technical Problem

A respiratory pattern of a human greatly varies depending on activity state such as being at rest, elaboration and sleep. Thus, even adoption of a method to judge a start of an inspiratory phase using the pressure gradient threshold may suffer a frequent sensing error of the start of an inspiratory phase due to a change in the activity state of the user, which is one of the problems in using a demand regulator function.

The present invention is based on the above consideration, and thus aims to provide a respiratory gas supply device that is equipped with a demand regulator function to detect exactly a respiration phase of a user and supply an inhalation gas in synchronization with a respiratory cycle.

Solution to Problem

The present invention includes the following embodiments of (1)-(18).

(1) The respiratory gas supply device of the present invention is a respiratory gas supply device of a respiration-synchronization type to supply a respiratory gas in response to a respiratory cycle of a user comprising: a pressure sensor for measuring pressure in a gas flow path, and a control unit for selecting one pressure gradient threshold from predetermined multiple pressure gradient thresholds, wherein the control unit judges a point at which a pressure gradient calculated from a signal of the pressure sensor becomes larger in the absolute value than the one pressure gradient threshold selected as an inspiration sensing point and supplies the respiratory gas for a certain period of time from the inspiration sensing point, and switches the one pressure gradient threshold to any one of the multiple pressure gradient thresholds based on a frequency of the inspiration sensing point during a predetermined time.

(2) The respiratory gas supply device according to (1), wherein the multiple pressure gradient thresholds include at least two pressure gradient thresholds of a first pressure gradient threshold and a second pressure gradient threshold that is smaller in the absolute value than the first pressure gradient threshold, and when the one pressure gradient threshold is selected and the frequency is less than a first frequency, the control unit switches the one pressure gradient threshold to a pressure gradient threshold that is smaller in the absolute value than the selected pressure gradient threshold, and when the one pressure gradient threshold is selected and the frequency is larger than a second frequency, the control unit switches the one pressure gradient threshold to a pressure gradient threshold that is larger in the absolute value than the selected pressure gradient threshold.

(3) The respiratory gas supply device according to (2), wherein the first pressure gradient threshold is −2.4 Pa/20 ms or larger and −1.0 Pa/20 ms or smaller, and the second pressure gradient threshold is −0.8 Pa/20 ms or larger and −0.1 Pa/20 ms or smaller.

(4) The respiratory gas supply device according to (2) or (3), wherein the first frequency is equivalent to a frequency of 1 to 8 times per 60 seconds.

(5) The respiratory gas supply device according to (2) or (3), wherein the second frequency is equivalent to a frequency of 48 to 60 times per 60 seconds.

(6) The respiratory gas supply device according to any one of (2) to (5), wherein, when the second pressure gradient threshold is selected as the one pressure gradient threshold and the frequency is smaller than a third frequency, the control unit switches the respiratory gas supply to a continuous supply for a certain period of time or a pulsative supply of a certain cycle regardless of the respiration phase of the patient.

(7) The respiratory gas supply device according to (6), wherein the third frequency is equivalent to a frequency of 1 to 10 times per 60 seconds.

(8) The respiratory gas supply device of the present invention is a respiratory gas supply device of a respiration-synchronization type to supply a respiratory gas in response to a respiratory cycle of a user comprising: a pressure sensor for measuring pressure in a gas flow path, and a control unit for selecting one pressure gradient threshold from predetermined multiple pressure gradient thresholds, wherein the control unit judges a point at which a pressure gradient calculated from a signal of the pressure sensor becomes larger in the absolute value than the one pressure gradient threshold selected as an inspiration sensing point and supplies the respiratory gas for a certain period of time from the inspiration sensing point, and switches the one pressure gradient threshold selected to any one of the multiple pressure gradient thresholds based on a time span between the latest two inspiration sensing points.

(9) The respiratory gas supply device according to (8), wherein the multiple pressure gradient thresholds include at least two pressure gradient thresholds of a first pressure gradient threshold and a second pressure gradient threshold that is smaller in the absolute value than the first pressure gradient threshold, and when the one pressure gradient threshold is selected and the time span is longer than a first time span, the control unit switches the one pressure gradient threshold to a pressure gradient threshold that is smaller in the absolute value than the selected pressure gradient threshold, and when the one pressure gradient threshold is selected and the time span is shorter than a second time span, the control unit switches the one pressure gradient threshold to a pressure gradient threshold that is larger in the absolute value than the selected pressure gradient threshold.

(10) The respiratory gas supply device according to (9), wherein the first time span is longer than 7.5 seconds.

(11) The respiratory gas supply device according to (9), wherein the second time span is shorter than 1.2 seconds.

(12) The respiratory gas supply device according to any one of (1) to (11), wherein the respiratory gas is a concentrated oxygen and the respiratory gas supply device is an oxygen concentration device.

(13) The control method of the present invention is a control method for a respiratory gas supply device of a respiration-synchronization type to supply a respiratory gas in response to a respiratory cycle of a user comprising: a pressure gradient threshold selection step of selecting one pressure gradient threshold from predetermined multiple pressure gradient thresholds, an inspiration sensing point detection step of detecting a point at which a pressure gradient calculated from a signal of the pressure sensor for sensing the respiratory cycle becomes larger in the absolute value than the one pressure gradient threshold selected in the pressure gradient threshold selection step, and a pressure gradient threshold switching step of switching the one pressure gradient threshold to any one of the multiple pressure gradient thresholds based on a frequency of the inspiration sensing point during a predetermined time.

(14) The control method for a respiratory gas supply device according to (13), further comprising a step of pulsatively supplying the respiratory gas for a certain period of time after detecting an inspiration sensing point in the inspiration sensing point detection step.

(15) The control method for a respiratory gas supply device according to (13) or (14), wherein the multiple pressure gradient thresholds include at least two pressure gradient thresholds of a first pressure gradient threshold and a second pressure gradient threshold that is smaller in the absolute value than the first pressure gradient threshold, and the pressure gradient threshold switching step, when the one pressure gradient threshold is selected and the frequency is less than a first frequency, switches the one pressure gradient threshold to a pressure gradient threshold that is smaller in the absolute value than the selected pressure gradient threshold, and when the one pressure gradient threshold is selected and the frequency is larger than a second frequency, switches the one pressure gradient threshold to a pressure gradient threshold that is larger in the absolute value than the selected pressure gradient threshold.

(16) The control method of the present invention is a control method for a respiratory gas supply device of a respiration-synchronization type to supply a respiratory gas in response to a respiratory cycle of a user comprising: a pressure gradient threshold selection step of selecting one pressure gradient threshold from predetermined multiple pressure gradient thresholds, an inspiration sensing point detection step of detecting a point at which a pressure gradient calculated from a signal of the pressure sensor for sensing the respiratory cycle becomes larger in the absolute value than the one pressure gradient threshold selected, and a pressure gradient threshold switching step of switching the one pressure gradient threshold to any one of the multiple pressure gradient thresholds based on a time span between the latest two inspiration sensing points.

(17) The control method for a respiratory gas supply device according to (16), further comprising a step of pulsatively supplying the respiratory gas for a certain period of time after detecting an inspiration sensing point in the inspiration sensing point detection step.

(18) The control method for a respiratory gas supply device according to (16) or (17), wherein the multiple pressure gradient thresholds include at least two pressure gradient thresholds of a first pressure gradient threshold and a second pressure gradient threshold that is smaller in the absolute value than the first pressure gradient threshold, and the pressure gradient threshold switching step, when the one pressure gradient threshold is selected and the time span is longer than a first time span, switches the one pressure gradient threshold to a pressure gradient threshold that is smaller in the absolute value than the selected pressure gradient threshold, and when the one pressure gradient threshold is selected and the time span is shorter than a second time span, switches the one pressure gradient threshold to a pressure gradient threshold that is larger in the absolute value than the selected pressure gradient threshold.

Advantageous Effects of Invention

In accordance with the present invention, a respiratory gas supply device can be provided that is equipped with a demand regulator function to sense exactly a respiration phase of a user and supply an inhalation gas in synchronization with a respiratory cycle.

BRIEF DESCRIPTION OF DRAWINGS

FIG. 1 is a configuration diagram of the demand regulator function of the respiratory gas supply device.

FIG. 2 is a flowchart of switching a pressure gradient threshold.

FIG. 3 is a flowchart of switching a pressure gradient threshold including manual switching.

FIG. 4 is a flowchart including switching to an auto-continuous supply of a respiratory gas.

FIG. 5 is a flowchart including switching to an auto-pulsative supply of a respiratory gas.

FIGS. 6(a) and 6(b) are set of graphs schematically illustrating respiratory patterns during an awake state and an asleep state.

DESCRIPTION OF EMBODIMENTS

Embodiments of the present invention is explained below with reference to Figs.

FIGS. 6(a) and 6(b) schematically illustrates respiratory patterns of a human during an awake state and an asleep state. Usually, respiration becomes shallow during sleep, and thus the respiratory pattern (FIG. 6(b)) during an asleep state has a smaller pressure amplitude than the respiratory pattern (FIG. 6(a)) during an awake state, and a pressure gradient during a transition from an expiratory phase to an inspiratory phase is also smaller. Note that a pressure gradient during a transition from an expiratory phase to an inspiratory phase in the respiratory pattern is always zero or smaller. In the present invention, the magnitude of a pressure gradient means the magnitude of an absolute value of the pressure gradient.

In the respiratory pattern in FIGS. 6(a) and 6(b), a pressure gradient threshold (hereinafter may be referred to as "threshold A") is set to, for example, $-2.0$ Pa/20 ms, and the inspiration sensing point G is assigned to a point where a pressure gradient measured using a pressure sensor is larger in the absolute value than threshold A, and the inspiration sensing point G is judged as a start of an inspiratory phase. In the respiratory pattern during an awake state in FIG. 6(a), just after shifting from an expiratory phase to an inspiratory phase, the pressure gradient becomes a maximum gradient of $-4.0$ Pa/20 ms, and thus is larger in the absolute value than threshold A, which enables sensing the start of the inspiratory phase as inspiration sensing point G.

On the other hand, in the respiratory pattern during an asleep state in FIG. 6(b), the respiration is shallow and slower compared with an awake state, and thus the pressure gradient is $-1.0$ Pa/20 ms at largest and rarely larger in the absolute value than threshold A. Thus, the inspiration sensing point G is not detected, which easily causes a sensing error of the start of an inspiratory phase. At this moment, re-setting of threshold A to, for example, $-0.2$ Pa/20 ms raises the sensitivity and enables detection of inspiration sensing point G even under a maximum gradient of $-1.0$ Pa/20 ms. However, if threshold A adjusted for an asleep state is used during an awake state, the sensitivity is too high such that a noise of the pressure sensor caused by a vibration in carrying the respiratory gas supply device, a slight body motion, and the like is mistaken as a pressure change, resulting in a frequent occurrence of false sensing of inspiration sensing point G.

In the demand regulator function of the respiratory gas supply device of the embodiment, pressure gradient thresholds suitable for an awake state (threshold $A_1$, threshold $A_2$ and threshold $A_3$) and a threshold suitable for an asleep state (threshold $A_4$) are predetermined, and the control unit of the respiratory gas supply device has a function to judge, based on a frequency of inspiration sensing point G during a predetermined time, whether the user is awake or asleep and whether the start of the inspiratory phase can be sensed appropriately, and then to switch the threshold between threshold $A_1$, threshold $A_2$, threshold $A_3$ and threshold $A_4$.

FIG. 1 is a diagram illustrating a principal configuration of the demand regulator function of the respiratory gas supply device. In the Fig., the solid line represents a gas flow path and the dotted line represents a path of electric signal. Respiratory gas supply source 1 is, for example, an oxygen concentrator, an oxygen cylinder, and the like, and supplies a gas for inhalation under a predetermined pressure and concentration. Control valve 6 is an electromagnetic valve and the like and is opened and closed by a signal from control unit 5. A gas supplied from respiratory gas supply source 1 is supplied to a user from cannula 2 by opening/closing of control valve 6 controlled by control unit 5. In gas supply path 3 connecting control valve 6 and cannula 2, pressure sensor 4 is equipped.

In the demand regulator function, pressure sensor 4 constantly measures pressure in gas supply path 3, which fluctuates by the respiration of the user, and sends the measured value to control unit 5. Control unit 5 detects inspiration sensing point G from a real-time respiratory pattern obtained by pressure sensor 4, judges the inspiration sensing point G as a start of an inspiratory phase, opens control valve 6, supplies a respiratory gas to cannula 2 at a certain flow rate only for a certain period of time, and then closes control valve 6. Considering that the oxygen administered after the first 60% of an inspiration phase stays generally in the dead space and is not involved in a gas exchange in the pulmonary alveoli, and that a respiratory rate of the patients is usually about 8 to 48 bpm, in order to surely use up the almost all amount of the supplied oxygen for an oxygen exchange in the pulmonary alveoli, it is desirable to complete the oxygen supply within about 0.24 to 1.2 seconds after the detection of inspiration sensing point G.

While controlling control valve 6, control unit 5 judges whether switching of threshold A used for detection of the inspiration sensing point G is necessary based on a frequency of inspiration sensing point G detected during a predetermined time. More specifically, based on a frequency of inspiration sensing point G detected during a predetermined time, control unit 5 selects any one of thresholds suitable for an awake state (threshold $A_1$, threshold $A_2$ and threshold $A_3$) and a threshold suitable for an asleep state (threshold $A_4$), and switches threshold A to the selected threshold.

FIG. 2 illustrates the flow in which control unit 5 judges whether switching of threshold A is necessary or not, and switches threshold A to threshold $A_1$, threshold $A_2$, threshold $A_3$ or threshold $A_4$.

When the device is started and the demand regulator function is activated, control unit 5 sets threshold A to threshold $A_1$ that has the lowest sensitivity in the pressure gradient thresholds suitable for an awake state (step S1). As for threshold $A_1$, threshold $A_2$, and threshold $A_3$, the respiratory patterns during an awake state of multiple HOT (Home Oxygen Therapy) patients are measured and examined, and the following results are found such that the thresholds are preferably in the range of −2.4 Pa/20 ms to −1.0 Pa/20 ms, and more preferably threshold $A_1$ is about −4.0 Pa/20 ms, threshold $A_2$ is about −2.0 Pa/20 ms, and threshold $A_3$ is about −1.0 Pa/20 ms. Also, as for threshold $A_4$, the respiratory patterns during an asleep state of multiple HOT patients are measured and examined, and the following results are found such that in order to keep the ratio (sensing ratio) of the frequency of inspiration sensing point G to the actual frequency of respiration at 75% or higher, threshold $A_4$ is preferably −0.8 Pa/20 ms to −0.1 Pa/20 ms, and more preferably about −0.2 Pa/20 ms. When threshold $A_1$, threshold $A_2$, and threshold $A_3$ are larger than −2.4 Pa/20 ms or when threshold $A_4$ is larger than −0.8 Pa/20 ms, these thresholds make the sensitivity insufficient for processing the respiratory patterns of the patients each during awake state and asleep state, respectively, and thus the sensing ratio of the frequency of inspiration sensing point G to the actual frequency of respiration becomes less than 75%, which does not allow a supply of the respiratory gas sufficient to keep the oxygen saturation in blood (SpO2) of the user at 90% or more, a general appropriate level.

On the other hand, when threshold $A_1$, threshold $A_2$, and threshold $A_3$ are smaller than −1.0 Pa/20 ms or when threshold $A_4$ is smaller than −0.1 Pa/20 ms, the sensing ratio of the inspiration sensing point G to the actual frequency of respiration is 130% or more. Specifically, the ratio of detecting noise of pressure sensor 4 mistakenly as the inspiration sensing point G becomes large, which does not allow a supply of the respiratory gas in synchronization with the start of the inspiratory phase, resulting in discomfort of the user and an increase in the respiratory gas consumption.

Control unit 5 detects inspiration sensing point G from threshold $A_1$ set in step S1 and a pressure gradient determined from a signal of pressure sensor 4, and starts a pulsative supply of the respiratory gas in synchronization with the start of the inspiratory phase.

Then, control unit 5 counts a frequency of inspiration sensing point G detected during predetermined period of time and judges whether switching is necessary from threshold $A_1$ to threshold $A_2$, from threshold $A_2$ to threshold $A_3$, and from threshold $A_3$ to threshold $A_4$ (step S2, S5, S8). The switches from threshold $A_1$ to threshold $A_2$, from threshold $A_2$ to threshold $A_3$, and from threshold $A_3$ to threshold $A_4$ are judged based on a criterion of whether a frequency of inspiration sensing point G sensed during the latest predetermined time $t_{up}$ sec from the start of measurement is less than $n_{up}$. Since a respiratory rate of a human is usually about 8 to 48 bpm, in the case where, for example, a frequency of inspiration sensing point G sensed during the latest 30 sec is less than 4 times (equivalent to 8 bpm) (($t_{up}$, $n_{up}$)=(30, 4)), the present threshold A (threshold $A_1$, threshold $A_2$ or threshold $A_3$) probably does not allow a correct sensing of inspiration sensing point G. Thus, when $n_{up}$ is less than 4 times per 30 seconds, control unit 5 switches threshold A to a threshold having one-level higher sensitivity of threshold $A_2$, threshold $A_3$ or threshold $A_4$ (step S3, S6, S9).

A predetermined time $t_{up}$ for counting the number of inspiration sensing point G $n_{up}$ is preferably 90 seconds or shorter. In addition, a combination of $t_{up}$ and $n_{up}$ as a criterion for the judgement can be any combination of ($t_{up}$, $n_{up}$) as well as the above-mentioned combination of ($t_{up}$, $n_{up}$)=(30, 4) as long as the combination satisfies the condition equivalent to 1 to 8 times per 60 seconds. (e.g., ($t_{up}$, $n_{up}$)=(15, 1), (15, 2), (30, 1), (30, 2), (30, 3), (60, 1), (60, 2), (60, 3), (60, 4), (60, 5), (60, 6), (60, 7), (60, 8), (90, 4), (90, 5), (90, 6), (90, 7), (90, 8), (90, 9), (90, 10), (90, 11), (90, 12), etc.). When $n_{up}$ per 60 seconds is more than 8 times, though the respiration is correctly sensed, threshold A is probably switched to a threshold with a higher sensitivity unnecessarily, and frequent switching of the threshold is caused by a false sensing of inspiration sensing point G due to a disturbance such as body motion and the like, which discomforts the user. On the other hand, when $n_{up}$ per 60 seconds is less than once, though inspiration sensing is deficient, the switching of threshold is delayed, threshold A with excessively low sensitivity to the present perspiration pattern of the patient is left unswitched, which does not allow a sufficient supply of the respiratory gas to the user and thus lowers the therapeutic effect by the respiratory gas supply device.

When a pressure gradient threshold is switched to threshold $A_4$ that is suitable for an asleep state in step S9, control unit 5 detects a point at which the pressure gradient is larger in the absolute value than threshold $A_4$ as inspiration sensing point G from a respiratory pattern measured with pressure sensor 4, and then pulsatively supplies the respiratory gas. The switching of threshold A to threshold $A_4$ enables detection of the start point of an inspiration phase during an asleep state that is unlikely to be detected based on threshold $A_1$ to $A_3$.

When threshold $A_2$, threshold $A_3$ or threshold $A_4$ is selected, control unit 5 counts the number of inspiration sensing point G detected during a predetermined period of time and judges whether switching is necessary from threshold $A_4$ to threshold $A_3$, from threshold $A_3$ to threshold $A_2$, or from threshold $A_2$ to threshold $A_1$ (step S4, S7, S10). The switching from threshold $A_4$ to threshold $A_3$, from threshold $A_3$ to threshold $A_2$, or from threshold $A_2$ to threshold $A_1$ is judged based on a criterion of whether the frequency of inspiration sensing point G sensed during the latest predetermined time $t_{down}$ sec from the start of measurement is larger than $n_{down}$. As mentioned above, since a respiratory rate of a human is usually about 8 to 48 bpm, in the case where, for example, the frequency of inspiration sensing point G sensed during the latest 5 sec is more than 4 times (equivalent to 48 bpm) (($t_{down}$, $n_{down}$)=(5, 4)), the present condition for detecting inspiration sensing point G using threshold A (threshold $A_2$, threshold $A_3$ or threshold $A_4$) probably allows a false sensing of a noise as inspiration sensing point G due to an excessively high sensitivity. Thus, when $n_{down}$ is more than 4 times per 5 seconds, control unit 5 switches threshold A to a threshold having one-level lower sensitivity such as threshold $A_3$, threshold $A_2$ or threshold $A_1$ (step S1, S3, S6).

A predetermined time $t_{down}$ for counting the number of inspiration sensing point G $n_{down}$ is preferably 60 seconds or shorter. In addition, a combination of $t_{down}$ and $n_{down}$ as a criterion for the judgement can be any combination of ($t_{down}$, $n_{down}$) as well as the above-mentioned combination of ($t_{down}$, $n_{down}$)=(5, 4) as long as the combination satisfies the condition equivalent to 48 to 60 times per 60 seconds. (e.g., ($t_{down}$, $n_{down}$)=(15, 12), (15, 13), (15, 14) (15, 15), (30, 24), (30, 25), (30, 26), (30, 27), (30, 28), (30, 29) (30, 30), (60, 48), (60, 49), (60, 50), (60, 51), (60, 52), (60, 53), (60, 54), (60, 55), (60, 56), (60, 57), (60, 58), (60, 59), (60, 60), etc.). When $n_{down}$ per 60 seconds is less than 48 times, though the respiration is correctly sensed, threshold A is probably switched to a threshold with a lower sensitivity unnecessarily, which does not allow a correct sensing of the respiration of the patient and a sufficient supply of the respiratory gas to the user and thus lowers the therapeutic effect by the respiratory gas supply device. On the other hand, when $n_{down}$ per 60 seconds is more than 60 times, though a false sensing of inspiration sensing point G occurs due to a disturbance such as body motion and the like, threshold A with excessively high sensitivity for the present respiratory pattern of the patient is left unswitched, which allows a pulsative supply of the respiratory gas at the timing other than inspiration, and thus the user likely feels discomfort.

As mentioned above, control unit 5 performs control of the demand regulator function in response to the state of the patient while switching between threshold $A_1$, threshold $A_2$, threshold $A_3$ and threshold $A_4$ based on a frequency $n_{up}$ of inspiration sensing point G detected during the latest period of the predetermined time $t_{up}$ and a frequency $n_{down}$ of inspiration sensing point G detected during the latest period of the predetermined time $t_{down}$, and thus can sense the start of an inspiratory phase correctly and supply a respiratory gas in synchronization with a respiratory cycle.

Besides, threshold $A_1$, threshold $A_2$, threshold $A_3$ and threshold $A_4$ can be switched based on a time span between the times of the latest two inspiration sensing point G. More specifically, when a time span between the times of the latest two inspiration sensing points G is longer than the predetermined time span $t_1$, control unit 5 judges that the respiration is not sensed correctly and switches threshold A to another threshold A having a higher sensitivity. On the contrary, when a time span between the times of the latest two inspiration sensing points G is shorter than the predetermined time span $t_2$, control unit 5 judges that a disturbance such as body motion and the like is sensed by mistake and switches threshold A to another threshold A having a lower sensitivity. At this time, considering that a respiratory rate of a human is usually about 8 to 48 bpm, desirably, $t_1$ is longer than 7.5 seconds, and $t_2$ is shorter than 1.2 seconds.

In addition, in the above description as an example of embodiments, though four levels of threshold are exemplified as switchable levels of a pressure gradient threshold A, any number of levels can be adopted as long as threshold A is used in the method mentioned above.

In the respiratory gas supply device of the embodiment of FIG. 1, a user can send a sensitivity switch signal to control unit 5 from user interface 7 and manually switch between threshold $A_1$, threshold $A_2$, threshold $A_3$ and threshold $A_4$. FIG. 3 is a flowchart exemplifying that a manual operation by a user can be performed for switching sensitivity.

When the device is started, and the demand regulator function is activated, control unit 5 sets threshold A to threshold $A_1$ (step S11). When the user pushes the sensitivity up button of user interface 7 (step S12), the control goes to step S14, and threshold $A_1$ is switched to threshold $A_2$. Similarly in the case of $A_2/A_3$ for threshold A (step S14/S19), when the sensitivity up button is pushed (step S15/S20), the control goes to step S19/step S24, and threshold A is switched to $A_3/A_4$. On the other hand, when the user pushes the sensitivity down button (step S16) while the respiratory gas supply device is operated using threshold $A_2$, the control goes to step S11, and the threshold A is switched to $A_1$. Similarly in the case of $A_3/A_4$ for threshold A (step S19/S24), when the sensitivity down button is pushed (step S21/S25), the control goes to step S14/step S19, and threshold A is switched to $A_2/A_3$. In the example in FIG. 3, the operation of the sensitivity switch button by the user switches the pressure gradient thresholds in preference to the judgment by control unit 5 based on frequencies $n_{up}$ and $n_{down}$ of inspiration sensing point G.

FIG. 4 is a flowchart exemplifying a safety function to continuously supply the respiratory gas only for about 90 seconds independent of a respiration phase in addition to a pulsed supply of the respiratory gas in synchronization with a respiration phase. The flow up to step S40 is the same as step S1 to 10 of FIG. 2. In step S40, when the frequency of inspiration sensing point G during 5 seconds is four times or less, in step S41, it is checked whether the frequency of inspiration sensing point G during the period of the latest predetermined timer $t_{backup}$ sec is less than $n_{backup}$, and it is confirmed whether the minimum respiratory rate during an asleep state is sensed.

As mentioned above, since a respiratory rate of a human is usually about 8 to 48 bpm, in the case where, for example, the frequency of inspiration sensing point G sensed during the latest 30 sec is less than 4 times (equivalent to 8 bpm) (($t_{backup}$, $n_{backup}$)=(30, 4)), the frequency of inspiration sensing point G is small, and the respiratory gas is probably not sufficiently supplied, even if the control unit controls using threshold $A_4$ having high sensitivity. Thus, control unit 5 switches a supply method of the respiratory gas to a continuous supply (auto-continuous flow) (step S42). According to FIG. 1, during the continuous supply of the respiratory gas, control valve 6 keeps an open state and pressure sensor 4 outputs a pressure of the respiratory gas as a sensed pressure, during which a pressure fluctuation due to respiration thus cannot be sensed. Thus, it is required to periodically stop the continuous supply of the respiratory gas and confirm whether the respiration of the user has recovered to an intensity that can be sensed sufficiently, and for this purpose, control unit 5 switches threshold A back to $A_4$ and re-starts detection of inspiration sensing point G after passing a certain time from the start of a supply of the auto-continuous flow (step S45). According to the examination of the inventors, based on the measurements and consideration of the respiratory patterns of the asleep states of multiple HOT patients, it has been found that, by setting the supply time of auto-continuous flow at 10 to 120 seconds, 75% or more of the whole respiration time becomes available to inspiration of the respiratory gas, and the supply time is further preferably about 90 seconds.

FIG. 5 is a flowchart exemplifying a safety function to pulsatively supply the respiratory gas independent of a respiration phase at a constant cycle in addition to a pulsed supply of the respiratory gas in synchronization with a respiration phase. The flow up to step S61 is the same as step S31 to 41 of FIG. 4.

Control unit 5 switches the supply method of the respiratory gas, instead of supplying an auto-continuous flow (step S42 of FIG. 4), to a pulsative supply (auto-pulse) (step S62) at a constant cycle (e.g., 50 bpm). During the period of this auto-pulse operation, control unit 5 continues the detection of inspiration sensing point G using threshold $A_4$, and cancels an auto-pulsative supply when inspiration sensing point G is detected again (step S65).

A predetermined time $t_{backup}$ for counting the number of inspiration sensing points G $n_{backup}$ is preferably 30 seconds or shorter. In addition, a combination of $t_{backup}$ and $n_{backup}$ as a criterion for the judgement can be any combination of ($t_{backup}$, $n_{backup}$) as well as the above-mentioned combination of ($t_{backup}$, $n_{backup}$)=(30, 4) as long as the combination satisfies the condition equivalent to 1 to 8 times per 60 seconds. (e.g., ($t_{backup}$, $n_{backup}$)=(15, 1), (15, 2), (30, 1), (30, 2), (30, 3), (60, 1), (60, 2), (60, 3), (60, 4), (60, 5), (60, 6), (60, 7), (60, 8), (90, 4), (90, 5), (90, 6), (90, 7), (90, 8), (90, 9), (90, 10), (90, 11), (90, 12), etc.). When $n_{backup}$ per 60 seconds is more than 8 times, though the respiration is sensed at the sensing ratio (the ratio of the frequency of inspiration sensing point G with respect to the actual frequency of respiration) of 75% or more at threshold $A_4$, a supply of the respiratory gas in auto-continuous flow or in auto-pulse is unnecessarily started. Though an oxygen supply in an auto-continuous flow or an auto-pulse can reduce the risk of decrease in oxygen saturation in blood of the patients compared with no supply, these methods do not necessarily satisfy sufficiently the amount of oxygen required by the patient, considering that the automatic supply of the respiratory gas in these methods is provided regardless of the respiratory pattern of the patient. Thus, use of an oxygen concentrator as a respiratory gas supply device may probably lower the therapeutic effect. Therefore, when an inspiration is sensed appropriately and the amount of oxygen required by the patient is supplied sufficiently, the unnecessary switching to an auto-continuous flow or an auto-pulse is desirably avoided. On the other hand, when $n_{backup}$ is less than once, inspiration sensing point G is hardly sensed, and thus supply of an auto-continuous flow or auto-pulse is delayed. Under these conditions, sufficient supply of the respiratory gas to the user during an asleep state is hindered and thus the therapeutic effect by the respiratory gas supply device is decreased. In addition, when the condition for switching to an auto-continuous flow or auto-pulse (step S41 or step S61) is satisfied five times per 30 minutes (step S43 or step S63), some sort of abnormality is judged to have probably occurred in the user or the respiratory gas supply device and an alarm is sounded (step S44 or step S64).

In the flow of FIGS. 4 and 5, even when inspiration sensing point G can be hardly sensed and thus the demand regulator function cannot supply the respiratory gas sufficiently, the risk to the user in feeling suffocation is reduced, since the respiratory gas is automatically supplied with supply of an auto-continuous flow or auto-pulse.

Though a preferred embodiment of the present invention was explained in detail as above, the present invention is not limited to the embodiment mentioned above, and various kinds of variation and modification are possible within the contents of the present invention described in the scope of claims.

INDUSTRIAL APPLICABILITY

In accordance with the present invention, a respiratory gas supply device equipped with a demand regulator function can be provided, wherein a control unit of the respiratory gas supply device switches a pressure gradient threshold for sensing the start of an inspiration phase in response to the state of a user, thus senses exactly a respiration phase, and supplies an inhalation gas in synchronization with a respiratory cycle.

REFERENCE SIGNS LIST

1. Respiratory gas supply source
2. Cannula
3. Gas supply path
4. Pressure sensor
5. Control unit
6. Control valve
7. User interface

The invention claimed is:

1. A respiratory gas supply device of a respiration-synchronization type to supply a respiratory gas in response to a respiratory cycle of a user comprising:
    a pressure sensor configured to measure pressure in a gas flow path; and
    a control unit configured to control a supply of the respiratory gas for a certain period of time from an inspiration sensing point that is detected by the control unit based on determining that a pressure gradient, during a transition from an expiratory phase to an inspiratory phase, is less than a pressure gradient threshold,
    wherein the control unit is further configured to determine the pressure gradient based on a signal from the pressure sensor,
    wherein the control unit is further configured to select, from multiple pressure gradient thresholds, the pressure gradient threshold based on a frequency of inspiration sensing points including the inspiration sensing point, and
    wherein the multiple pressure gradient thresholds are less than zero.

2. The respiratory gas supply device according to claim 1, wherein the multiple pressure gradient thresholds include at least two pressure gradient thresholds of a first pressure gradient threshold and a second pressure gradient threshold that is larger than the first pressure gradient threshold, and
    when the one pressure gradient threshold is selected and the frequency is less than a first frequency, the control unit is configured to switch the one pressure gradient threshold to a pressure gradient threshold that is larger than the selected pressure gradient threshold, and
    when the one pressure gradient threshold is selected and the frequency is larger than a second frequency, the control unit is configured to switch the one pressure gradient threshold to a pressure gradient threshold that is smaller than the selected pressure gradient threshold.

3. The respiratory gas supply device according to claim 2, wherein the first pressure gradient threshold is −2.4 Pa/20 ms or larger and −1.0 Pa/20 ms or smaller, and the second pressure gradient threshold is −0.8 Pa/20 ms or larger and −0.1 Pa/20 ms or smaller.

4. The respiratory gas supply device according to claim 2, wherein the first frequency is equivalent to a frequency of 1 to 8 times per 60 seconds.

5. The respiratory gas supply device according to claim 2, wherein the second frequency is equivalent to a frequency of 48 to 60 times per 60 seconds.

6. The respiratory gas supply device according to claim 2, wherein, when the second pressure gradient threshold is selected as the one pressure gradient threshold and the frequency is smaller than a third frequency, the control unit is configured to switch the respiratory gas supply to a continuous supply for a certain period of time or a pulsative supply of a certain cycle.

7. The respiratory gas supply device according to claim 6, wherein the third frequency is equivalent to a frequency of 1 to 10 times per 60 seconds.

8. The respiratory gas supply device according to claim 1, wherein the respiratory gas is a concentrated oxygen and the respiratory gas supply device is an oxygen concentration device.

9. A respiratory gas supply device of a respiration-synchronization type to supply a respiratory gas in response to a respiratory cycle of a user comprising:
    a pressure sensor configured to measure pressure in a gas flow path; and
    a control unit configured to control a supply of the respiratory gas for a certain period of time from an inspiration sensing point that is detected by the control unit based on determining that a pressure gradient, during a transition from an expiratory phase to an inspiratory phase, is less than a pressure gradient threshold, wherein the control unit is further configured to determine the pressure gradient based on a signal from the pressure sensor, wherein the control unit is further configured to select, from multiple pressure gradient thresholds, the pressure gradient threshold based on a time span between a latest two of inspiration sensing points including the inspiration sensing point, and wherein the multiple pressure gradient thresholds are less than zero.

10. The respiratory gas supply device according to claim 9, wherein the multiple pressure gradient thresholds include at least two pressure gradient thresholds of a first pressure gradient threshold and a second pressure gradient threshold that is larger than the first pressure gradient threshold, and when the one pressure gradient threshold is selected and the time span is longer than a first time span, the control unit is configured to switch the one pressure gradient threshold to a pressure gradient threshold that is larger than the selected pressure gradient threshold, and when the one pressure gradient threshold is selected and the time span is shorter than a second time span, the control unit is configured to switch the one pressure gradient threshold to a pressure gradient threshold that is smaller than the selected pressure gradient threshold.

11. The respiratory gas supply device according to claim 10, wherein the first time span is longer than 7.5 seconds.

12. The respiratory gas supply device according to claim 10, wherein the first time span is shorter than 1.2 seconds.

13. A control method for a respiratory gas supply device of a respiration-synchronization type to supply a respiratory gas in response to a respiratory cycle of a user comprising:

controlling a supply of the respiratory gas for a certain period of time from an inspiration sensing point that is detected by the control unit based on determining that a pressure gradient, during a transition from an expiratory phase to an inspiratory phase, is less than a pressure gradient threshold;

determining the pressure gradient based on a signal from the pressure sensor; and selecting, from multiple pressure gradient thresholds, the pressure gradient threshold based on a frequency of inspiration sensing points including the inspiration sensing point, wherein the multiple pressure gradient thresholds are less than zero.

14. The control method for a respiratory gas supply device according to claim 13, further comprising a step of pulsatively supplying the respiratory gas for a certain period of time after detecting an inspiration sensing point in the inspiration sensing point detection step.

15. The control method for a respiratory gas supply device according to claim 13, wherein the multiple pressure gradient thresholds include at least two pressure gradient thresholds of a first pressure gradient threshold and a second pressure gradient threshold that is larger than the first pressure gradient threshold, and the pressure gradient threshold switching step, when the one pressure gradient threshold is selected and the frequency is less than a first frequency, switches the one pressure gradient threshold to a pressure gradient threshold that is larger than the selected pressure gradient threshold, and when the one pressure gradient threshold is selected and the frequency is larger than a second frequency, switches the one pressure gradient threshold to a pressure gradient threshold that is smaller than the selected pressure gradient threshold.

16. A control method for a respiratory gas supply device of a respiration-synchronization type to supply a respiratory gas in response to a respiratory cycle of a user comprising:

controlling a supply of the respiratory gas for a certain period of time from an inspiration sensing point that is detected by the control unit based on determining that a pressure gradient, during a transition from an expiratory phase to an inspiratory phase, is less than a pressure gradient threshold;

determining based on a signal from the pressure sensor; and selecting, from multiple pressure gradient thresholds, the pressure gradient threshold based on a time span between a latest two of inspiration sensing points including the inspiration sensing point, wherein the multiple pressure gradient thresholds are less than zero.

17. The control method for a respiratory gas supply device according to claim 16, further comprising a step of pulsatively supplying the respiratory gas for a certain period of time after detecting an inspiration sensing point in the inspiration sensing point detection step.

18. The control method for a respiratory gas supply device according to claim 16, wherein the multiple pressure gradient thresholds include at least two pressure gradient thresholds of a first pressure gradient threshold and a second pressure gradient threshold that is larger than the first pressure gradient threshold, and the pressure gradient threshold switching step, when the one pressure gradient threshold is selected and the time span is longer than a first time span, switches the one pressure gradient threshold to a pressure gradient threshold that is larger than the selected pressure gradient threshold, and when the one pressure gradient threshold is selected and the time span is shorter than a second time span, switches the one pressure gradient threshold to a pressure gradient threshold that is smaller than the selected pressure gradient threshold.

* * * * *